(12) United States Patent
Baumgart

(10) Patent No.: US 7,199,162 B1
(45) Date of Patent: Apr. 3, 2007

(54) USE OF TREOSULFAN FOR PATIENT CONDITIONING BEFORE BONE MARROW OR BLOOD STEM CELL TRANSPLANTATION

(75) Inventor: Joachim Baumgart, Appen (DE)

(73) Assignee: Medac Gesellschaft fur Klinische Spezialpraparate mbH, Hamburg (DE)

( * ) Notice: Subject to any disclaimer, the term of this patent is extended or adjusted under 35 U.S.C. 154(b) by 343 days.

(21) Appl. No.: 10/129,352

(22) PCT Filed: Nov. 3, 2000

(86) PCT No.: PCT/EP00/10871

§ 371 (c)(1),
(2), (4) Date: Sep. 23, 2002

(87) PCT Pub. No.: WO01/32154

PCT Pub. Date: May 10, 2001

(30) Foreign Application Priority Data

Nov. 5, 1999 (DE) .................... 199 53 517

(51) Int. Cl.
A61K 31/10 (2006.01)
A61K 31/675 (2006.01)
A61K 31/66 (2006.01)
(52) U.S. Cl. .................... 514/711; 514/79; 514/110
(58) Field of Classification Search ............. 514/711, 514/79, 110
See application file for complete search history.

(56) References Cited

OTHER PUBLICATIONS

Carter, Stephan K., M.D. et al.; Chemotherapy of Cancer, Second Edition, (1981); A Wiley & Sons, New York, New York; pp. 362-365.*
Ploemacher, et al., Treosulfan as an Alternative Conditioning Agent in Bone Marrow Transplantation, Nov. 15, 1999, Blood, 94, 10 Suppl. 1 pt. 2, p. 324b.*
Parkman, et al., Busulfan and Total Body Irradiation as Antihematopoietic Stem Cell Agents in the Preparation of Patients with Congenital Bone Marrow Disorders for Allogenic Bone Marrow Transplantation, 1984, Blood, 64(4), 852-7.*
Parfitt, K. Ed. Martindale: The Complete Drug Reference, 32nd edition, 1999, pp. 509-511, 516-517 and 568.*
Jabado, et al., Bone Marrow Transplantation from Genetically HLA-Nonidentical Donors in Children with Fatal Inherited Disorders Excluding Severe Combined Immunodeficiencies, 1996, Pediatrics, 98, 420-8.*
Hirabayashi, et al., Busulfan, Cyclophosphamide and Total Body Irradiation as Conditioning for Allogenic Bone Marrow Transplantation for Acute and Chronic Myeloid Leukemia, 1998, Bone Marrow Transplant, 21, 1079-83.*
Gulati et al., "Comparison of single-, double- or triple-exposure protocols for the rodent bone marrow/ peripheral blood micronucleus assay using 4-aminobiphenyl and treosulphan" *Mutation Research* 234: 135-139 (1990).

* cited by examiner

*Primary Examiner*—Shengjun Wang
(74) *Attorney, Agent, or Firm*—Needle & Rosenberg PC

(57) ABSTRACT

The invention relates to the use of treosulfan as a conditioning agent before allogenic transplantation of bone marrow or haematopoietic stem cells, whereby treosulfan is administered, either as single effective agent, or in combination with other chemotherapetic agents or immunosuppressant agents.

15 Claims, No Drawings

USE OF TREOSULFAN FOR PATIENT CONDITIONING BEFORE BONE MARROW OR BLOOD STEM CELL TRANSPLANTATION

The present invention relates to the use of treosulfan as a conditioning agent before allogenic transplantation of bone marrow or haematopoietic stem cells, whereby treosulfan is administered, either in combination with other chemotherapeutic agents or immunosuppressive agents, or as a single effective agent.

Before allogenic transplantation of bone marrow or haematopoietic stem cells, patients are subjected to "conditioning therapy" in order to:
a) eliminate the recipient's own blood-formation precursor cells (stem cells),
b) achieve immunosuppression in the recipient, which prevents acute rejection of the transplant, and
c) achieve a cytotoxic reduction of any malignantly degenerated cells still present in the recipient.

As an established means of conditioning, for example a combination of busultan and cyclophosphamide is administered before the donor's bone marrow or haematopoietic stem cells are transplanted.

A substantial risk of allogenic transplantation of bone marrow, besides the possibility of a derailing "Craft versus Host Reaction (CvHD), i.e. aggression of co-transferred reactive immunocells towards the recipient's organs, is the comparatively high toxicity of the preceding conditioning therapy. Although the side effects of this conditioning, in particular the high busulfan-associated morbidity and mortality are a considerable disadvantage of this therapy, which has been used for a long time, up to now no comparably effective alternatives with fewer side effects have been developed.

The task of the present invention is therefore to make available a conditioning therapy/conditioning agent, that does not have the disadvantages known in the state of the art.

The task is solved according to the invention by use of treosulfan as a conditioning agent. In particular the task is solved by the subject of the annexed patent claims.

Within the framework of the present invention, it has surprisingly been found that the serious disadvantages in connection with the toxicity of conventional conditionings can be avoided, if treosulfan is used as a conditioning agent before allogenic transplantation of bone marrow or haematopoietic stem cells (blood stem cells, preferably peripheral blood stem cells).

Treosulfan is the name given to L-treitol-1,4-bic-methanesulfonate, a dihydroxy derivative of the alkylating agent busulfan, which was first synthesised in 1961 and up to now has only been used as a conventionally dosed chemotherapeutic, for example in patients with ovarian carcinoma, administered orally or intravenously.

According to the invention, it has been found that treosulfan, for example instead of high doses of busulfan, can be effectively combined with chemotherapeutics and/or immunosuppressive agents, such as cyclophosphamide, carboplatin, thiotepa, melphalan, fludarabine, immunosuppressive antibodies, or whole-body irradiation in an advantageous manner, whereby the serious and sometimes fatal side-effects attributed to busulfan can be largely or completely avoided. In particular, the serious liver, lung, kidney and CNS toxicities associated with busulfan are not observed when treosulfan is used, even in high doses.

An essential advantage of treosulfan is its consistent high water-solubility in contrast to busulfan, which makes it possible to prepare infusion solutions. In contrast, busulfan, due to its low solubility is usually administered in the form of tablets whose resorption varies considerably in individual cases. As the oral administration of busulfan is, moreover, only poorly tolerated by many patients due to gastro-intestinal side-effects, it frequently results in vomiting, which has a considerable detrimental effect on reliable and reproducible bio-availability of, e.g., busulfan in individual cases. Intravenously administered busulfan-containing solutions, on the other hand, can be obtained only by means of solubilizers, such as, e.g. dimethylacetamide, which can themselves cause side-effects.

In contrast, with treosulfan infusion solutions can be produced easily directly. Intravenous application enables precise dosing of active substance and safe application. In addition, it has surprisingly been found that with highly-dosed tresosulfan alone or in combination with, e.g. cyclophosphamide or fludarabine a successful and safe conditioning therapy with, at the same time, distinctly reduced side effects can be carried out. The total dose of treosulfan administered amounts to at least 20 g/m$^2$ body surface area and preferably lies within the range 20 to 60 g/m$^2$.

According to the invention, it is therefore possible to replace the conventional conditioning with, e.g. busulfan/cyclophosphamide by conditioning using treosulfan/cyclophosphamide or treosulfan/fludarabine. For example, 3×14 to 16 g treosulfan/m$^2$ body surface area (corresponding to a total dose of 42 to 48 g/m$^2$) are administered on three consecutive days. Then 60–100 mg cyclophosphamide/kg body weight are infused on the two following days.

Within the framework of the present invention it was further surprisingly found that treosulfan can also be used alone, as treosulfan in higher doses can eliminate not only primitive stem cells, but also "committed stem cells". In this way both busulfan and cyclophosphamide can be replaced by treosulfan alone, in which case the serious and sometimes fatal side-effects of busulfan and/or cyclophosphamide observed with conventional conditioning therapy do not occur.

For conditioning therapy with treosulfan as the only active substance, at least 20 g treosulfan/m$^2$ body surface area are required, preferably 20 to approx. 60 g/m$^2$, advantageously 30 g/m$^2$ and especially preferably 42 to 48 g treosulfan/m$^2$ body surface area are administered as total dose for the patients to be treated. Treosulfan can be applied either as a single dose or over a period of up to 1 week (7 days). With the single dose, a two hour infusion of the abovementioned total dose is possible, however, a continuous infusion can also take place over a period of up to 24 hours. If the conditioning is carried out over a period of, for example 2 to 7 days (e.g. over 3, 5 or 7 days), daily infusions over a period of 0.5 to 24 hours are possible. The total of the daily individual doses corresponds to the above-mentioned total dose of treosulfan, in which case the daily quantities of active substance applied may be identical to, or different from, each other. It is also possible to carry out conditioning within the framework of a continuous infusion over e.g. 3, 5 or 7 days.

The present invention thus relates to the use of treosulfan for the production of a pharmaceutical composition for conditioning therapy (conditioning agent) before allogenic transplantation of bone marrow or haematopoietic stem cells, whereby treosulfan is administered either alone or together (in combination) with other chemotherapeutics and/or immunosuppressive agents (e.g. cyclophosphamide, fludarabine, thiotepa, melphalan, carboplatin, immunosuppressive antibodies, whole-body irradiation etc.). This means that treosulfan is used either as a single active substance or in combination with at least one further chemotherapeutic agent and/or immunosuppressive agents to produce a conditioning agent/conditioning drug, wherein the pharmaceutical composition is especially suitable for conditioning therapy with additional whole-body irradiation of the patient.

In the case of the pharmaceutical composition which contains treosulfan and at least one further chemotherapeutic agent and/or immunosuppressive agents, this is a combination preparation which is present either in the form of a formulation comprising all the active substances, or in a packaging unit, which contains the active substances in spatially separated formulations (in separate containers), i.e. in the form of a treosulfan-containing pharmaceutical composition and of a pharmaceutical composition (spatially separated therefrom) containing at least the chemotherapeutic agent and/or immunosuppressive agents. Correspondingly the active substances in the abovementioned combination preparations are administered either simultaneously or at intervals before transplantation of bone marrow or stem cells.

The present invention therefore, in addition to the use of treosulfan as a single active substance for the preparation of a conditioning agent, also relates to combination preparations which contain treosulfan and at least one further chemotherapeutic agent and/or immunosuppressive agents. The details concerning the use (administration) of treosulfan, including combination with other active substances (in particular with cyclophosphamide) have already been mentioned above. The pharmaceutical compounds and combination preparations are correspondingly formulated in such a way, and contain the active ingredients mentioned in each case in such concentrations, that they are suitable for administration of the abovementioned quantities of active substances over the periods of time indicated.

Compared with busulfan, treosulfan, in spite of an identical DNA alkylation sites, possibly due to its different alkylation mechanism possesses comparable effectiveness, but a considerably reduced side-effects potential. Thus treosulfan shows significant stem cell toxicity, both towards primitive stem cells and also towards "committed stem cells"; whilst, in contrast to busulfan, it has only a slight non-haematological toxicity profile and in particular no significant liver, kidney, CNS or lung toxicity.

Due to its high water-solubility treosulfan can easily be administered intravenously and exhibits reliable and linear pharmacokinetic properties.

The invention is described below with reference to examples.

EXAMPLES

It was investigated whether treosulfan has stem-cell toxic properties with regard to bone marrow comparable with those of busulfan, both active substances being administered in a maximally tolerated dose in a murine bone-marrow transplantation model.

The recipient mice (BG-Gpi-$1^b$) were treated with 3×2500 mg/kg or 7500 mg/kg (corresponding to 22.5 g/m$^2$) treosulfan or 50 mg/kg busulfan. 24 hours after administration the elimination of the different haematopoietic stem cells in the host bone marrow was ascertained using the in vitro cobblestone area forming cell assays (CAFC; cf. Ploemacher et al., Blood 78 (1991) 2527–2533).

The daily fractionation of the fairly high doses of treosulfan administered (3×2500 mg/kg) surprisingly led to effective elimination of both the primitive and also the "committed" progenitor cells by 3 to 5 powers of ten.

Treosulfan administered in fractionated doses was also evaluated in an H-2-compatible allogenic bone-marrow transplantation trial (C.B10→B6). In this trial, an immunological reaction resulting in rejection of the transplant must be prevented by conditioning with e.g. treosulfan, before growth of the transplant is possible. In this case, treosulfan along was able to induce an almost complete and stable donor-type chimerism in the recipient. On the other hand, busulfan along was unable to bring about effective conditioning of the test animals before allogenic bone-marrow transplantation. Rather, additional administrations of e.g. cyclophosphamide were needed to effect a sufficient immuno-suppression, to prevent transplant rejection and to induce full donor type chimerism.

What is claimed is:

1. A method for treating a patient with conditioning therapy pior to allogenic transplantation of bone marrow or hematopoietic stem cells, comprising the step of administering a total dose of Treosulfan of at least 20 g/(m$^2$ body surface area) over a period of 2 to 7 days.
2. The method of claim 1, wherein the total dose is 20 to 60 g/(m$^2$ body surface area).
3. The method of claim 1, wherein the total dose is 30 g/(m$^2$ body surface area).
4. The method of claim 1, wherein the total dose is 42 to 48 g/(m$^2$ body surface area).
5. The method of claim 1, wherein the period is selected from the group consisting of 3, 5 and 7 days.
6. The method of claim 1, wherein the dose is administered by continuous infusion.
7. The method of claim 1, wherein the dose is administered in daily individual doses.
8. The method of claim 1, wherein said Treosulfan is administered by infusion over a period of 2 to 7 days, in each case for a period of 0.5 to 24 hours per day.
9. The method of claim 1, further comprising the step of using at least one further chemotherapeutic agent or immunosuppressive agent.
10. The method of claim 9, wherein the Treosulfan is administered in a combination preparation.
11. The method of claim 9, wherein the chemotherapeutic agent is a cytostatic agent.
12. The method of claim 11, wherein the cytostatic agent is selected from the group consisting of cyclophosphamide, thiotepa, melphalan, carboplatin and fludarabine.
13. The method of claim 9, wherein the immunosuppressive agent is an immunosuppressive antibody.
14. The method of claim 9, further comprising the step of performing whole-body irradiation.
15. The method of claim 12, wherein the cytostatic agent is cyclophosphamide, wherein the Treosulfan is administered 14 to 16 g/(m$^2$ body surface area) on each of 3 consecutive days, and the cyclophosphamide is administered 60 to 100 mg/(kg body weight) on each of the following 2 days.

* * * * *